United States Patent
Grover et al.

(10) Patent No.: US 10,799,118 B2
(45) Date of Patent: Oct. 13, 2020

(54) MOTION TRACKING USING ELECTRONIC DEVICES

(71) Applicant: Intel Corporation, Santa Clara, CA (US)

(72) Inventors: Jaskaran S. Grover, Amritsar (IN); Venkat Natarajan, Bangalore (IN); Kumar Ranganathan, Bangalore (IN)

(73) Assignee: INTEL CORPORATION, Santa Clara, CA (US)

( * ) Notice: Subject to any disclaimer, the term of this patent is extended or adjusted under 35 U.S.C. 154(b) by 395 days.

(21) Appl. No.: 15/553,547

(22) PCT Filed: Feb. 16, 2016

(86) PCT No.: PCT/US2016/018071
§ 371 (c)(1),
(2) Date: Aug. 24, 2017

(87) PCT Pub. No.: WO2016/160150
PCT Pub. Date: Oct. 6, 2016

(65) Prior Publication Data
US 2018/0125362 A1    May 10, 2018

(30) Foreign Application Priority Data
Mar. 27, 2015    (IN) .......................... 1587/CHE/2015

(51) Int. Cl.
*A61B 5/11*    (2006.01)
*A61B 5/00*    (2006.01)
(Continued)

(52) U.S. Cl.
CPC .......... *A61B 5/0022* (2013.01); *A61B 5/1114* (2013.01); *G06F 3/011* (2013.01);
(Continued)

(58) Field of Classification Search
CPC ........ G06F 3/011; A61B 5/1114; G16H 20/30
See application file for complete search history.

(56) References Cited

U.S. PATENT DOCUMENTS

| 2002/0109512 A1 | 8/2002 | Chia et al. |
| 2006/0169021 A1 | 8/2006 | Silverstein |

(Continued)

FOREIGN PATENT DOCUMENTS

| CN | 107408151 A | 11/2017 |
| EP | 3274791 A1 | 1/2018 |

(Continued)

OTHER PUBLICATIONS

International Search Report and Written Opinion received for International Application No. PCT/US2016/018071, dated May 24, 2016, 14 pages.

(Continued)

*Primary Examiner* — Mohamed Charioui
*Assistant Examiner* — Christine Y Liao (57) ABSTRACT

In one example an input/output interface to receive motion tracking data from at least one remote motion sensing device and a controller coupled to the input/output interface and comprising logic, at least partially including hardware logic, to receive the motion tracking data, generate estimated position data using the motion tracking data; and present the estimated position data on a display device coupled to the electronic device. Other examples may be described.

17 Claims, 9 Drawing Sheets

(51) Int. Cl.
  *G06F 3/01* (2006.01)
  *G16H 20/30* (2018.01)
  *G16H 40/67* (2018.01)
(52) U.S. Cl.
  CPC ............... *G16H 20/30* (2018.01); *A61B 5/11* (2013.01); *A61B 5/7257* (2013.01); *A61B 5/742* (2013.01); *A61B 5/744* (2013.01); *A61B 2503/10* (2013.01); *G16H 40/67* (2018.01)

(56) References Cited

U.S. PATENT DOCUMENTS

| | | | |
|---|---|---|---|
| 2006/0279549 A1* | 12/2006 | Zhang | G06F 3/03545 345/173 |
| 2011/0172820 A1 | 7/2011 | Kim et al. | |
| 2012/0183156 A1 | 7/2012 | Schlessinger et al. | |
| 2012/0193156 A1 | 7/2012 | Schlessinger et al. | |
| 2014/0066816 A1 | 6/2014 | McNames et al. | |
| 2014/0275854 A1* | 9/2014 | Venkatraman | A61B 5/721 600/301 |
| 2014/0278215 A1 | 9/2014 | Keal et al. | |
| 2014/0288392 A1 | 9/2014 | Hong et al. | |
| 2016/0066820 A1* | 3/2016 | Sales | A61B 5/4076 600/595 |

FOREIGN PATENT DOCUMENTS

| | | |
|---|---|---|
| JP | 2007-330432 A | 12/2007 |
| JP | 2009-039466 A | 2/2009 |
| JP | 2010-0113343 A | 5/2010 |
| JP | 2013192590 A | 9/2013 |
| JP | 2014-526913 A | 10/2014 |
| JP | 6689877 B2 | 4/2020 |
| WO | 2013/112230 A1 | 8/2013 |
| WO | 2013112230 A1 | 8/2013 |
| WO | 2016/160150 A1 | 10/2016 |
| WO | 2016160150 A1 | 10/2016 |

OTHER PUBLICATIONS

International Search Report and Written Opinion for PCT Application No. PCT/US2016/018071, dated May 24, 2016, 12 pages.
Supplementary European Search Report for EP Application No. EP16773633, 9 pages.
Notification of Publication of CN 201680013178.7, Publication No. CN107408151A, dated Nov. 28, 2017 28 pages.
Notice of Publication received for Chinese Patent Application No. 201680013178.7, dated Dec. 6, 2017, 3 pages including 1 page of English Translation.
International Preliminary Report on Patentability received for International Application No. PCT/US2016/018071, dated Oct. 12, 2017, 11 pages.
Examination Report for Indian Application No. 1587/CHE/2015 dated Jul. 29, 2019, 6 pages.
Report Notice of Allowance for Japanese Application No. JP2017-550221, dated Mar. 23, 2020, 4 pages.

* cited by examiner

FIG. 1  Electronic Device 100

MOTION TRACKING USING ELECTRONIC DEVICES

This application claims priority under 35 U.S.C. § 371 to International Application No. PCT/US2016/018071 filed Feb. 16, 2016, entitled MOTION TRACKING USING ELECTRONIC DEVICES. The entire disclosure(s) of these documents are incorporated by reference herein for all purposes.

RELATED APPLICATIONS

The present application claims priority under 35 U.S.C. 365(b) to IN Application No. 1587/CHE/2015 filed on Mar. 27, 2015. Said Application No. 1587/CHE/2015 is hereby incorporated herein by reference in its entirety.

BACKGROUND

The subject matter described herein relates generally to the field of electronic devices and more particularly to motion tracking using electronic devices.

Motion tracking may be useful for various applications such as analyzing movement of body parts during athletic activity, physical therapy, location/position tracking and also object tracking applications. Thus, techniques which enable an electronic device to implement motion tracking based on inputs from remote sensors may find utility.

BRIEF DESCRIPTION OF THE DRAWINGS

The detailed description is described with reference to the accompanying figures.

DETAILED DESCRIPTION

Described herein are exemplary systems and methods to implement motion tracking in electronic devices. In the following description, numerous specific details are set forth to provide a thorough understanding of various examples. However, it will be understood by those skilled in the art that the various examples may be practiced without the specific details. In other instances, well-known methods, procedures, components, and circuits have not been illustrated or described in detail so as not to obscure the particular examples.

As described above, it may be useful to provide electronic devices with motion tracking algorithms and ingredients that may be used to implement techniques to track the motion of one or more motion sensors in communication with the electronic device. As described herein, one or more motion sensor assemblies may be incorporated into wearable apparatus such as bracelets, clothing, elastomeric bands or the like which may be worn by a user. Alternatively, one or more motion sensor assemblies may be adhered to or embedded into a body segment of a user. In operation the motion sensor assemblies may sample motion data generated by one or more motion sensors and apply a bias elimination algorithm to the motion data to generate a debiased motion data set from the samples. In some examples, the bias elimination algorithm may run on the device instead of the motion sensor assembly. A transmitter may then transmit the debiased motion data set for receipt by an electronic device communicatively coupled to the motion sensor assemblies.

The electronic device may comprise an input/output interface to receive motion tracking data from at least one remote motion sensing device and a controller coupled to the input/output interface. The controller may comprise of logic to receive the motion tracking data, generate estimated position data using the motion tracking data, and present/render the estimated position data on a display device coupled to the electronic device.

Additional features and operating characteristics of the magnetometer unit and of electronic devices are described below with reference to FIGS. 1-10.

Figure 1:
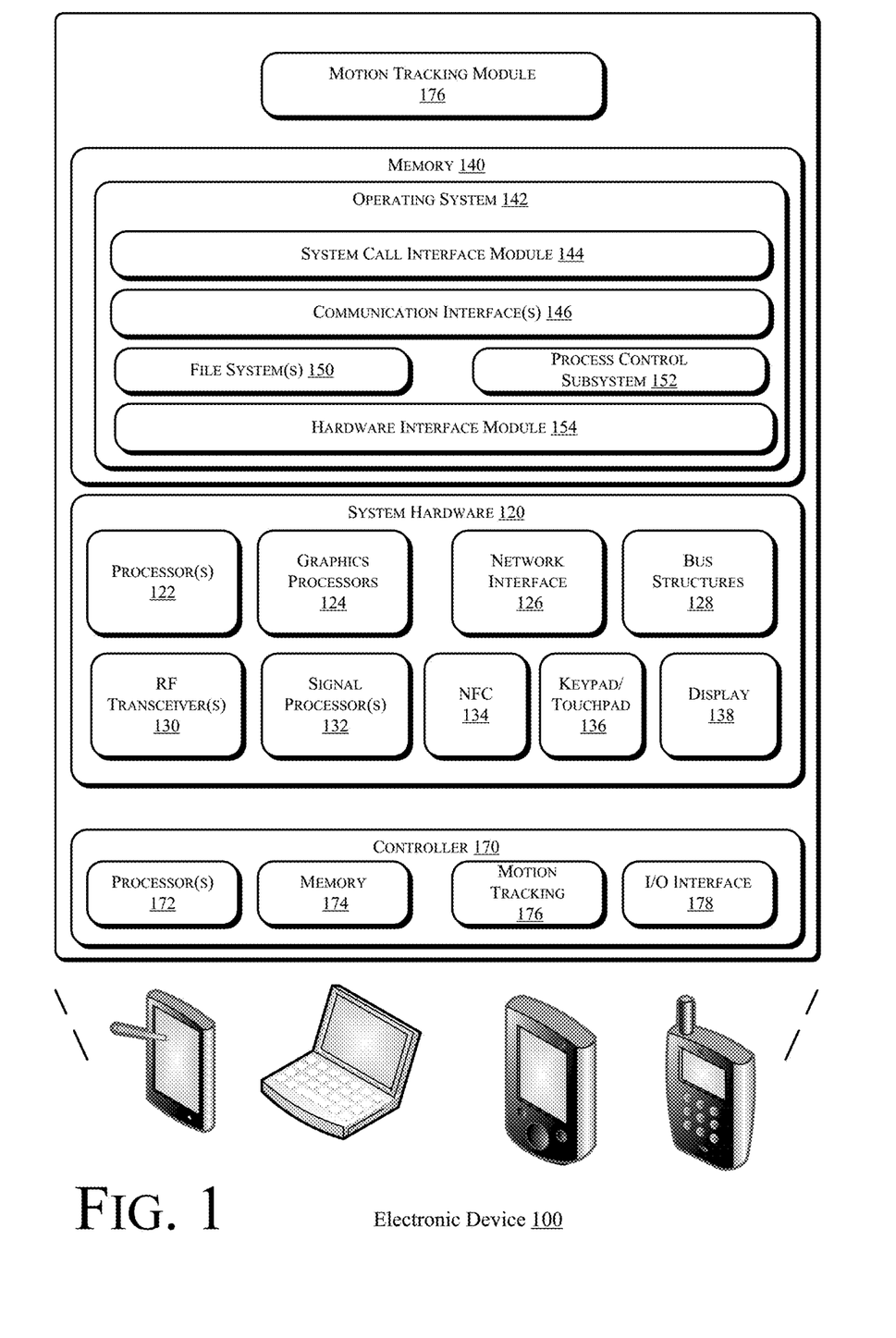
FIG. 1 is a schematic illustration of an electronic device which may be adapted to implement motion tracking in electronic devices in accordance with some examples.

FIG. 1 is a schematic illustration of an electronic device 100 which may be adapted to include a motion tracking module in accordance with some examples. In various examples, electronic device 100 may include or be coupled to one or more accompanying input/output devices including a display, one or more speakers, a keyboard, one or more other I/O device(s), a mouse, a camera, or the like. Other exemplary I/O device(s) may include a touch screen, a voice-activated input device, a track ball, a geolocation device, an accelerometer/gyroscope, biometric feature input devices, and any other device that allows the electronic device 100 to receive input from a user.

The electronic device 100 includes system hardware 120 and memory 140, which may be implemented as random access memory and/or read-only memory. A file store may be communicatively coupled to electronic device 100. The file store may be internal to electronic device 100 such as, e.g., eMMC, SSD, one or more hard drives, or other types of storage devices. Alternatively, the file store may also be external to electronic device 100 such as, e.g., one or more external hard drives, network attached storage, or a separate storage network.

System hardware 120 may include one or more processors 122, graphics processors 124, network interfaces 126, and bus structures 128. In one embodiment, processor 122 may be embodied as an Intel® Atom™ processors, Intel® Atom™ based System-on-a-Chip (SOC) or Intel® Core2 Duo® or i3/i5/i7 series processor available from Intel Corporation, Santa Clara, Calif., USA. As used herein, the term "processor" means any type of computational element, such as but not limited to, a microprocessor, a microcontroller, a complex instruction set computing (CISC) microprocessor, a reduced instruction set (RISC) microprocessor, a very long instruction word (VLIW) microprocessor, or any other type of processor or processing circuit.

Graphics processor(s) 124 may function as adjunct processor that manages graphics and/or video operations. Graphics processor(s) 124 may be integrated onto the motherboard of electronic device 100 or may be coupled via an expansion slot on the motherboard or may be located on the same die or same package as the Processing Unit.

In one embodiment, network interface 126 could be a wired interface such as an Ethernet interface (see, e.g., Institute of Electrical and Electronics Engineers/IEEE 802.3-2002) or a wireless interface such as an IEEE 802.11a, b or g-compliant interface (see, e.g., IEEE Standard for IT-Telecommunications and information exchange between systems LAN/MAN—Part II: Wireless LAN Medium Access Control (MAC) and Physical Layer (PHY) specifications Amendment 4: Further Higher Data Rate Extension in the 2.4 GHz Band, 802.11G-2003). Another example of a wireless interface would be a general packet radio service (GPRS) interface (see, e.g., Guidelines on GPRS Handset Requirements, Global System for Mobile Communications/ GSM Association, Ver. 3.0.1, December 2002), Bluetooth Low Energy (BTLE) protocols, or the like.

Bus structures 128 connect various components of system hardware 128. In one embodiment, bus structures 128 may be one or more of several types of bus structure(s) including a memory bus, a peripheral bus or external bus, and/or a local bus using any variety of available bus architectures including, but not limited to, 11-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Universal Serial Bus (USB), Advanced Graphics Port (AGP), Personal Computer Memory Card International Association bus (PCMCIA), and Small Computer Systems Interface (SCSI), a High Speed Synchronous Serial Interface (HSI), a Serial Low-power Inter-chip Media Bus (SLIM-bus®), or the like.

Electronic device 100 may include an RF transceiver 130 to transceive RF signals, a Near Field Communication (NFC) radio 134, and a signal processing module 132 to process signals received by RF transceiver 130. RF transceiver may implement a local wireless connection via a protocol such as, e.g., Bluetooth or 802.11X. IEEE 802.11a, b or g-compliant interface (see, e.g., IEEE Standard for IT-Telecommunications and information exchange between systems LAN/MAN—Part II: Wireless LAN Medium Access Control (MAC) and Physical Layer (PHY) specifications Amendment 4: Further Higher Data Rate Extension in the 2.4 GHz Band, 802.11G-2003). Another example of a wireless interface would be a WCDMA, LTE, general packet radio service (GPRS) interface (see, e.g., Guidelines on GPRS Handset Requirements, Global System for Mobile Communications/GSM Association, Ver. 3.0.1, December 2002).

Electronic device 100 may further include one or more input/output interfaces such as, e.g., a keypad 136 and a display 138. In some examples electronic device 100 may not have a keypad and use the touch panel for input.

Memory 140 may include an operating system 142 for managing operations of electronic device 100. In one embodiment, operating system 142 includes a hardware interface module 154 that provides an interface to system hardware 120. In addition, operating system 140 may include a file system 150 that manages files used in the operation of electronic device 100 and a process control subsystem 152 that manages processes executing on electronic device 100.

Operating system 142 may include (or manage) one or more communication interfaces 146 that may operate in conjunction with system hardware 120 to transceive data packets and/or data streams from a remote source. Operating system 142 may further include a system call interface module 144 that provides an interface between the operating system 142 and one or more application modules resident in memory 130. Operating system 142 may be embodied as a UNIX operating system or any derivative thereof (e.g., Linux, Android, etc.) or as a Windows® brand operating system, or other operating systems.

In some examples an electronic device may include a controller 170, which may comprise one or more controllers that are separate from the primary execution environment. The separation may be physical in the sense that the controller may be implemented in controllers which are physically separate from the main processors. Alternatively, the trusted execution environment may be logical in the sense that the controller may be hosted on same chip or chipset that hosts the main processors.

By way of example, in some examples the controller 170 may be implemented as an independent integrated circuit located on the motherboard of the electronic device 100, e.g., as a dedicated processor block on the same SOC die. In other examples the trusted execution engine may be implemented on a portion of the processor(s) 122 that is segregated from the rest of the processor(s) using hardware enforced mechanisms.

In the embodiment depicted in FIG. 1 the controller 170 comprises a processor 172, a memory module 174, a motion tracking module 176, and an I/O interface 178. In some examples the memory module 174 may comprise a persistent flash memory module and the various functional modules may be implemented as logic instructions encoded in the persistent memory module, e.g., firmware or software. The I/O module 178 may comprise a serial I/O module or a parallel I/O module. Because the controller 170 is separate from the main processor(s) 122 and operating system 142, the controller 170 may be made secure, i.e., inaccessible to hackers who typically mount software attacks from the host processor 122. In some examples portions of the motion tracking module 176 may reside in the memory 140 of electronic device 100 and may be executable on one or more of the processors 122.

Figure 2:
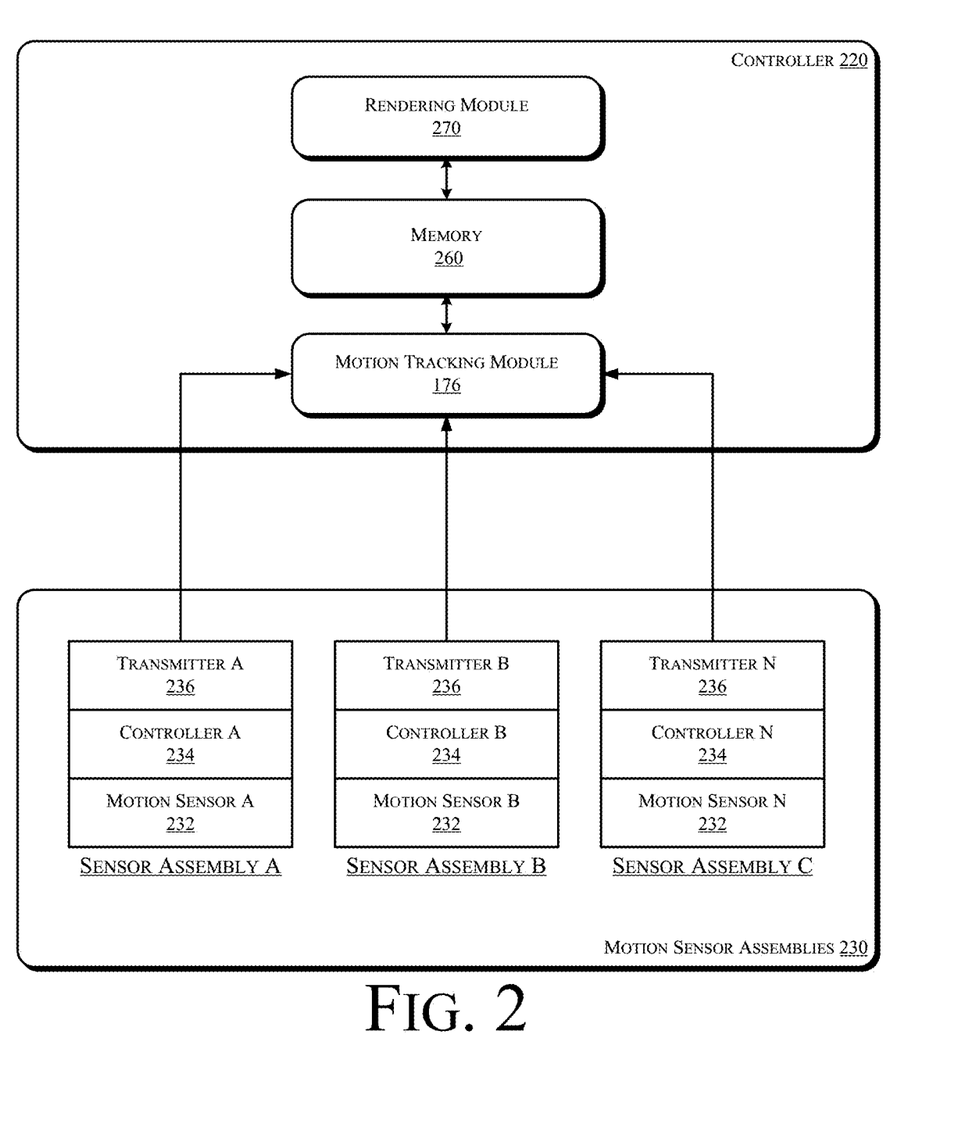
FIG. 2 is a high-level schematic illustration of an exemplary architecture to implement motion tracking in electronic devices in accordance with some examples.

In some examples the motion tracking module 176 interacts with one or more other components of the electronic device 100 to receive motion tracking data from one or more remote motion sensing assemblies and to process the motion tracking data. FIG. 2 is a high-level schematic illustration of an exemplary architecture to implement a motion tracking in electronic devices. Referring to FIG. 2, a controller 220 may be embodied as general purpose processor 122 or as a low-power controller such as controllers 170. Controller 220 may comprise a rendering module 270, a motion tracking module 176, and local memory 260. As described above, in some examples the rendering module 270 and motion tracking module 176, combiner unit 250 may be implemented as logic instructions executable on controller 220, e.g., as software or firmware, or may be reduced to hardwired logic circuits. Local memory 260 may be implemented using volatile and/or non-volatile memory.

One or more motion sensor assemblies 230 may be communicatively coupled to the motion tracking module, e.g., via a wired or wireless communication connection. The example depicted in FIG. 2 illustrates a number, N, of motion sensor assemblies illustrated as assembly A, B . . . N. The total number of assemblies, N, may vary between 1 and any large number of sensors. As described above, the motion sensors may be incorporated into wearable apparatus such as bracelets, clothing, elastomeric bands/patch or the like which may be worn by a user. Alternatively, one or more motion sensor assemblies may be adhered to or embedded into a body segment of a user.

The respective motion sensor assemblies 230 comprise a motion sensor 232, a controller 234, and a transmitter 236. The respective motion sensors 232 may be implemented as a gyroscope, inertial measurement unit, or the like. The respective controllers 234 may be implemented as an independent integrated circuit. The respective transmitters 236 may be implemented a wireless transmitters which operate according to any suitable wireless protocol.

Figure 3:
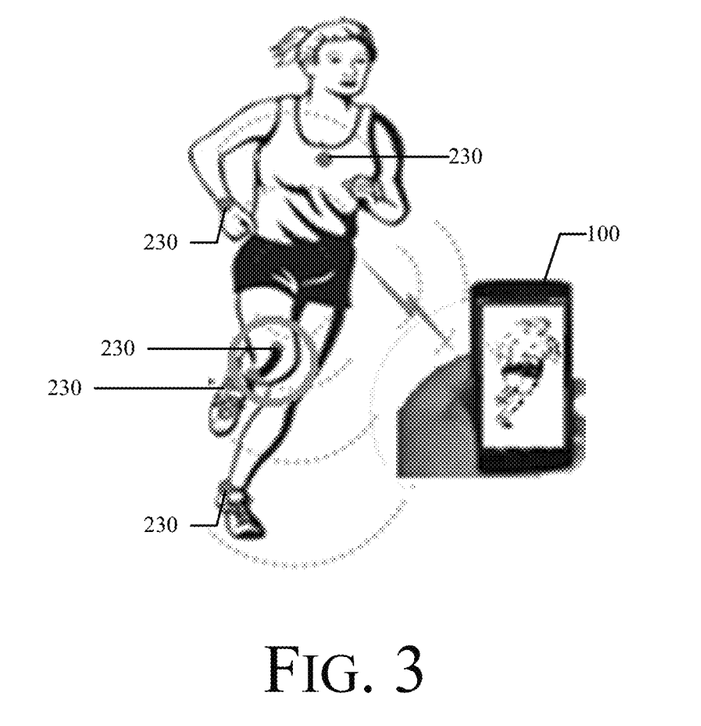
FIG. 3 is a schematic illustration of an environment in which motion tracking in electronic devices may be implemented in accordance with some examples.

FIG. 3 is a schematic illustration of an environment in which motion tracking in electronic devices may be implemented in accordance with some examples. Referring to FIG. 3, plurality of motion sensor assemblies 230 may be positioned on various locations of a user. The motion sensor assemblies 230 may be communicatively coupled to an electronic device 100.

Figure 4A:
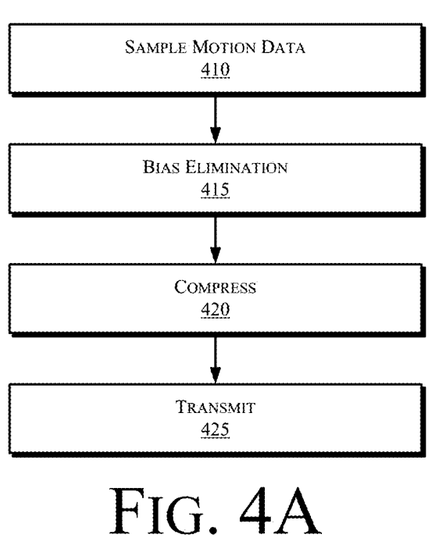
FIGS. 4A 4B and FIG. 5 are flowcharts illustrating operations in a method to implement motion tracking in electronic devices in accordance with some examples.
Figure 4B:
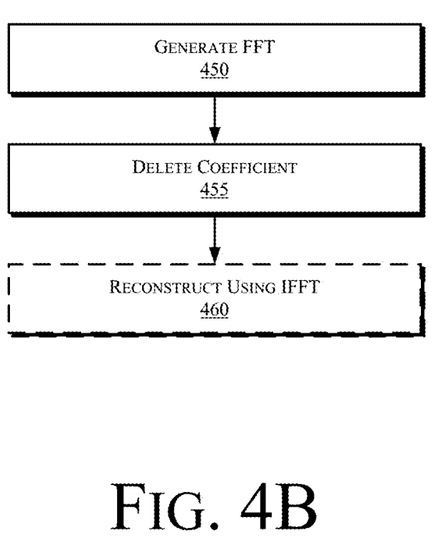
Figure 5:
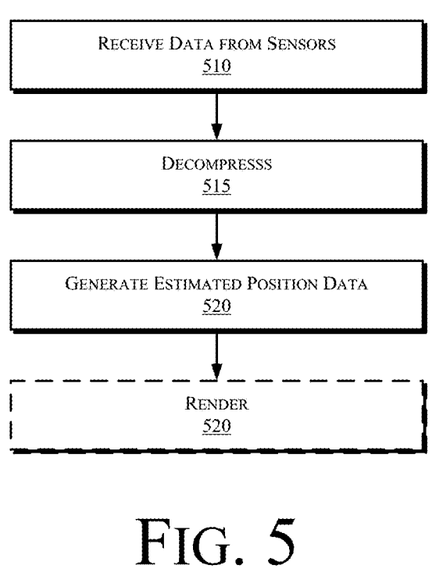

FIGS. 4A-4B and FIG. 5 are flowcharts illustrating operations in a method to implement motion tracking in electronic devices in accordance with some examples. In some examples the operations depicted in FIGS. 4A and 4B may be implemented by the respective motion sensor assemblies 230. Referring to FIG. 4A, at operation 410 the controller 234 samples data generated by the motion sensor 232 in response to movement of the motion sensor. In some examples the controller 234 samples motion data at a 20 Hz rate.

At operation 415 the controller 234 implements a bias elimination algorithm to the motion data to generate an unbiased motion data set. In some examples the algorithm uses a sample size of 400 samples for bias estimation. FIG. 4B is a flowchart illustrating operations in one example of the bias elimination algorithm. Referring to FIG. 4B, at operation 450 a fast fourier transform (FFT) of the sample data collected in operation 410 is determined. At operation 455 at least one coefficient of the FFT computed in operation 450 is deleted. In some examples the first coefficient of the FFT is deleted to generate a simplified FFT. At operation 460 the data set is reconstructed by determining the inverse fast fourier transform IFFT of the simplified FFT determined in operation 455.

The bias removal algorithm depicted in FIG. 4B provides a de-biased signal set from the sample collected in operation 410. Thus, bias need not be propagated in the state vector in the state estimation algorithms (e.g.: Kalman filter). A reduced dimensionality of the state vector reduces computation time by up to a factor of 5× compared to previous techniques. Furthermore, the debiased gyroscope signal also enables us to get an improved orientation estimation also known as attitude. Examples of attitude representations are Euler Angles, Quaternions and Rotation Matrices.

Referring back to FIG. 4A, at operation 420 the data set reconstructed in operation 460 may be compressed, and at operation 425 the data compressed data set is transmitted by transmitter 236.

FIG. 5 depicts operations implemented by the motion tracking module 176. Referring to FIG. 5, at operation 510 data transmitted by a sensor assembly in operation 425 is received. At operation 515 the data is decompressed, and at operation 520 estimated position data is generated. In some examples a Kalman Filter algorithm may be used to eliminate jitter in the motion data. At operation 520 the estimated position data may be presented on a display device coupled to the electronic device. In some examples the estimated position/orientation data may be presented to rendering module 270, which generates a motion video which comprises the estimated orientation of the user or object.

Figure 6:
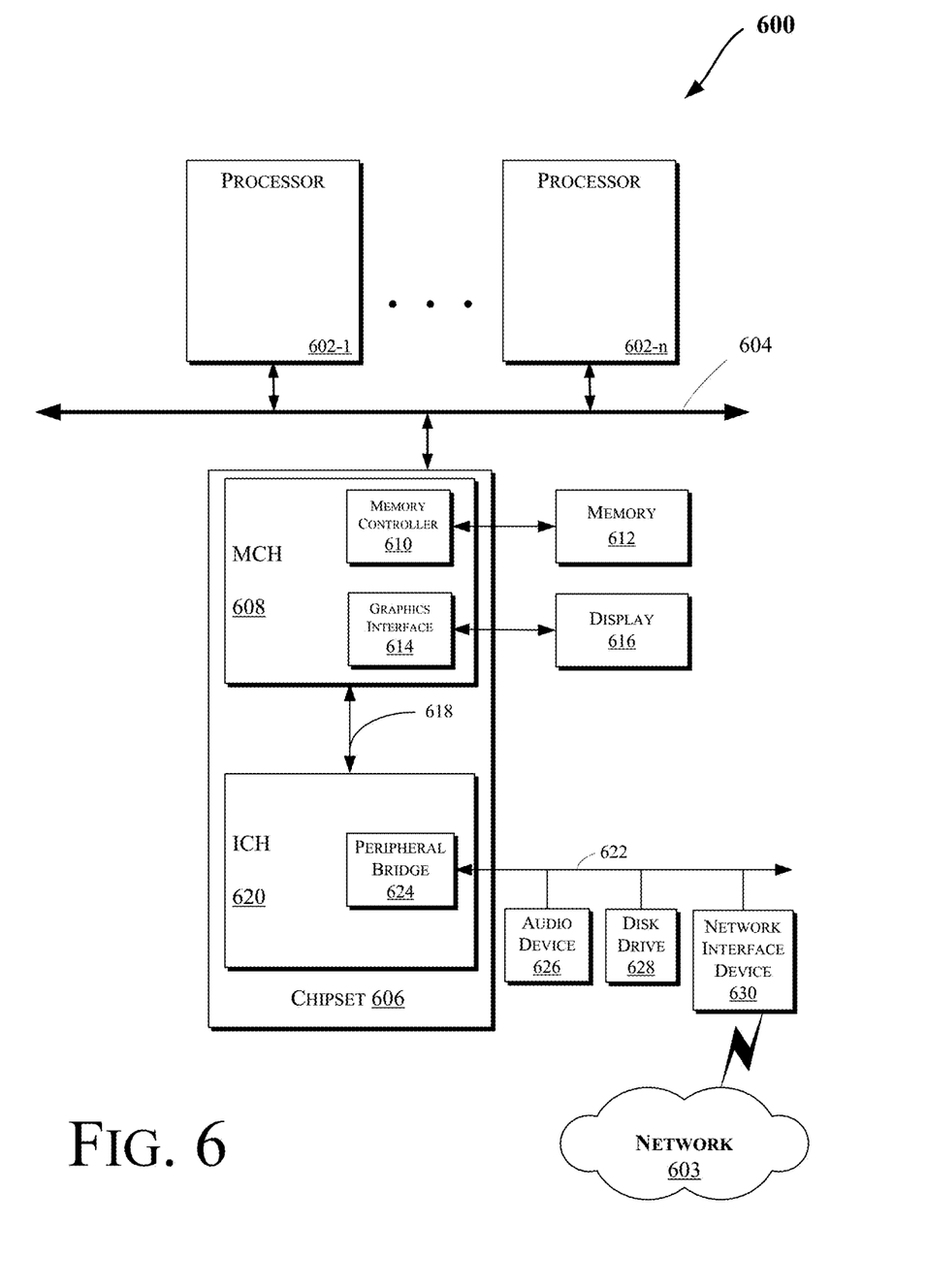
FIGS. 6-10 are schematic illustrations of electronic devices which may be adapted to implement motion tracking in electronic devices in accordance with some examples.

As described above, in some examples the electronic device may be embodied as a computer system. FIG. 6 illustrates a block diagram of a computing system 600 in accordance with an example. The computing system 600 may include one or more central processing unit(s) 602 or processors that communicate via an interconnection network (or bus) 604. The processors 602 may include a general purpose processor, a network processor (that processes data communicated over a computer network 603), or other types of a processor (including a reduced instruction set computer (RISC) processor or a complex instruction set computer (CISC)). Moreover, the processors 602 may have a single or multiple core design. The processors 602 with a multiple core design may integrate different types of processor cores on the same integrated circuit (IC) die. Also, the processors 602 with a multiple core design may be implemented as symmetrical or asymmetrical multiprocessors. In an example, one or more of the processors 602 may be the same or similar to the processors 102 of FIG. 1. For example, one or more of the processors 602 may include the control unit 120 discussed with reference to FIGS. 1-3. Also, the operations discussed with reference to FIGS. 3-5 may be performed by one or more components of the system 600.

A chipset 606 may also communicate with the interconnection network 604. The chipset 606 may include a memory control hub (MCH) 608. The MCH 608 may include a memory controller 610 that communicates with a memory 612 (which may be the same or similar to the memory 130 of FIG. 1). The memory 412 may store data, including sequences of instructions, that may be executed by the processor 602, or any other device included in the computing system 600. In one example, the memory 612 may include one or more volatile storage (or memory) devices such as random access memory (RAM), dynamic RAM (DRAM), synchronous DRAM (SDRAM), static RAM (SRAM), or other types of storage devices. Nonvolatile memory may also be utilized such as a hard disk. Additional devices may communicate via the interconnection network 604, such as multiple processor(s) and/or multiple system memories.

The MCH 608 may also include a graphics interface 614 that communicates with a display device 616. In one example, the graphics interface 614 may communicate with the display device 616 via an accelerated graphics port (AGP). In an example, the display 616 (such as a flat panel display) may communicate with the graphics interface 614 through, for example, a signal converter that translates a digital representation of an image stored in a storage device such as video memory or system memory into display signals that are interpreted and displayed by the display 616. The display signals produced by the display device may pass through various control devices before being interpreted by and subsequently displayed on the display 616.

A hub interface 618 may allow the MCH 608 and an input/output control hub (ICH) 620 to communicate. The ICH 620 may provide an interface to I/O device(s) that communicate with the computing system 600. The ICH 620 may communicate with a bus 622 through a peripheral bridge (or controller) 624, such as a peripheral component interconnect (PCI) bridge, a universal serial bus (USB) controller, or other types of peripheral bridges or controllers. The bridge 624 may provide a data path between the processor 602 and peripheral devices. Other types of topologies may be utilized. Also, multiple buses may communicate with the ICH 620, e.g., through multiple bridges or controllers. Moreover, other peripherals in communication with the ICH 620 may include, in various examples, integrated drive electronics (IDE) or small computer system interface (SCSI) hard drive(s), USB port(s), a keyboard, a mouse, parallel port(s), serial port(s), floppy disk drive(s), digital output support (e.g., digital video interface (DVI)), or other devices.

The bus 622 may communicate with an audio device 626, one or more disk drive(s) 628, and a network interface device 630 (which is in communication with the computer network 603). Other devices may communicate via the bus 622. Also, various components (such as the network interface device 630) may communicate with the MCH 608 in some examples. In addition, the processor 602 and one or more other components discussed herein may be combined to form a single chip (e.g., to provide a System on Chip (SOC)). Furthermore, the graphics accelerator 616 may be included within the MCH 608 in other examples.

Furthermore, the computing system 600 may include volatile and/or nonvolatile memory (or storage). For example, nonvolatile memory may include one or more of the following: read-only memory (ROM), programmable ROM (PROM), erasable PROM (EPROM), electrically EPROM (EEPROM), a disk drive (e.g., 628), a floppy disk, a compact disk ROM (CD-ROM), a digital versatile disk (DVD), flash memory, a magneto-optical disk, or other types of nonvolatile machine-readable media that are capable of storing electronic data (e.g., including instructions).

Figure 7:
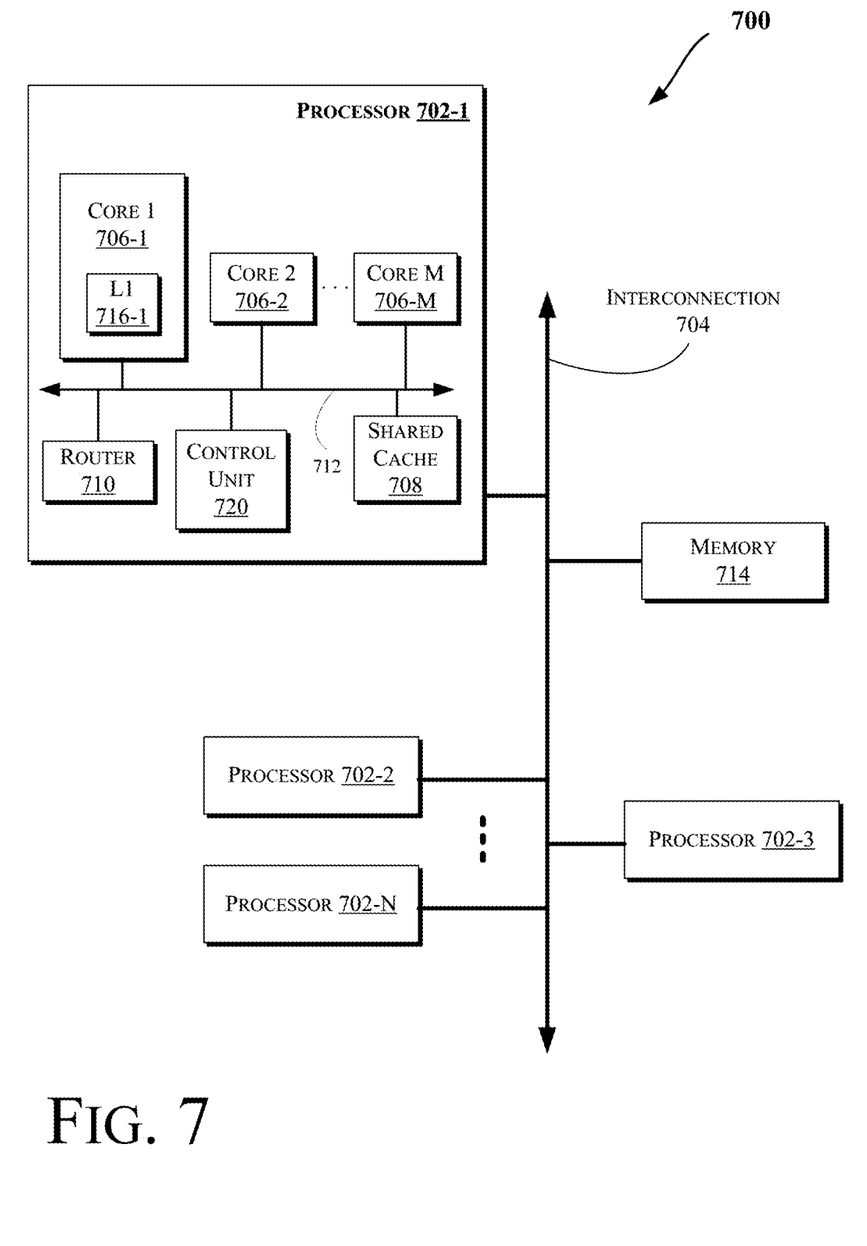

FIG. 7 illustrates a block diagram of a computing system 700, according to an example. The system 700 may include one or more processors 702-1 through 702-N (generally referred to herein as "processors 702" or "processor 702"). The processors 702 may communicate via an interconnection network or bus 704. Each processor may include various components some of which are only discussed with reference to processor 702-1 for clarity. Accordingly, each of the remaining processors 702-2 through 702-N may include the same or similar components discussed with reference to the processor 702-1.

In an example, the processor 702-1 may include one or more processor cores 706-1 through 706-M (referred to herein as "cores 706" or more generally as "core 706"), a shared cache 708, a router 710, and/or a processor control logic or unit 720. The processor cores 706 may be implemented on a single integrated circuit (IC) chip. Moreover, the chip may include one or more shared and/or private caches (such as cache 708), buses or interconnections (such as a bus or interconnection network 712), memory controllers, or other components.

In one example, the router 710 may be used to communicate between various components of the processor 702-1 and/or system 700. Moreover, the processor 702-1 may include more than one router 710. Furthermore, the multitude of routers 710 may be in communication to enable data routing between various components inside or outside of the processor 702-1.

The shared cache 708 may store data (e.g., including instructions) that are utilized by one or more components of the processor 702-1, such as the cores 706. For example, the shared cache 708 may locally cache data stored in a memory 714 for faster access by components of the processor 702. In an example, the cache 708 may include a mid-level cache (such as a level 2 (L2), a level 3 (L3), a level 4 (L4), or other levels of cache), a last level cache (LLC), and/or combinations thereof. Moreover, various components of the processor 702-1 may communicate with the shared cache 708 directly, through a bus (e.g., the bus 712), and/or a memory controller or hub. As shown in FIG. 7, in some examples, one or more of the cores 706 may include a level 1 (L1) cache 716-1 (generally referred to herein as "L1 cache 716"). In one example, the control unit 720 may include logic to implement the operations described above with reference to the memory controller 122 in FIG. 2.

Figure 8:
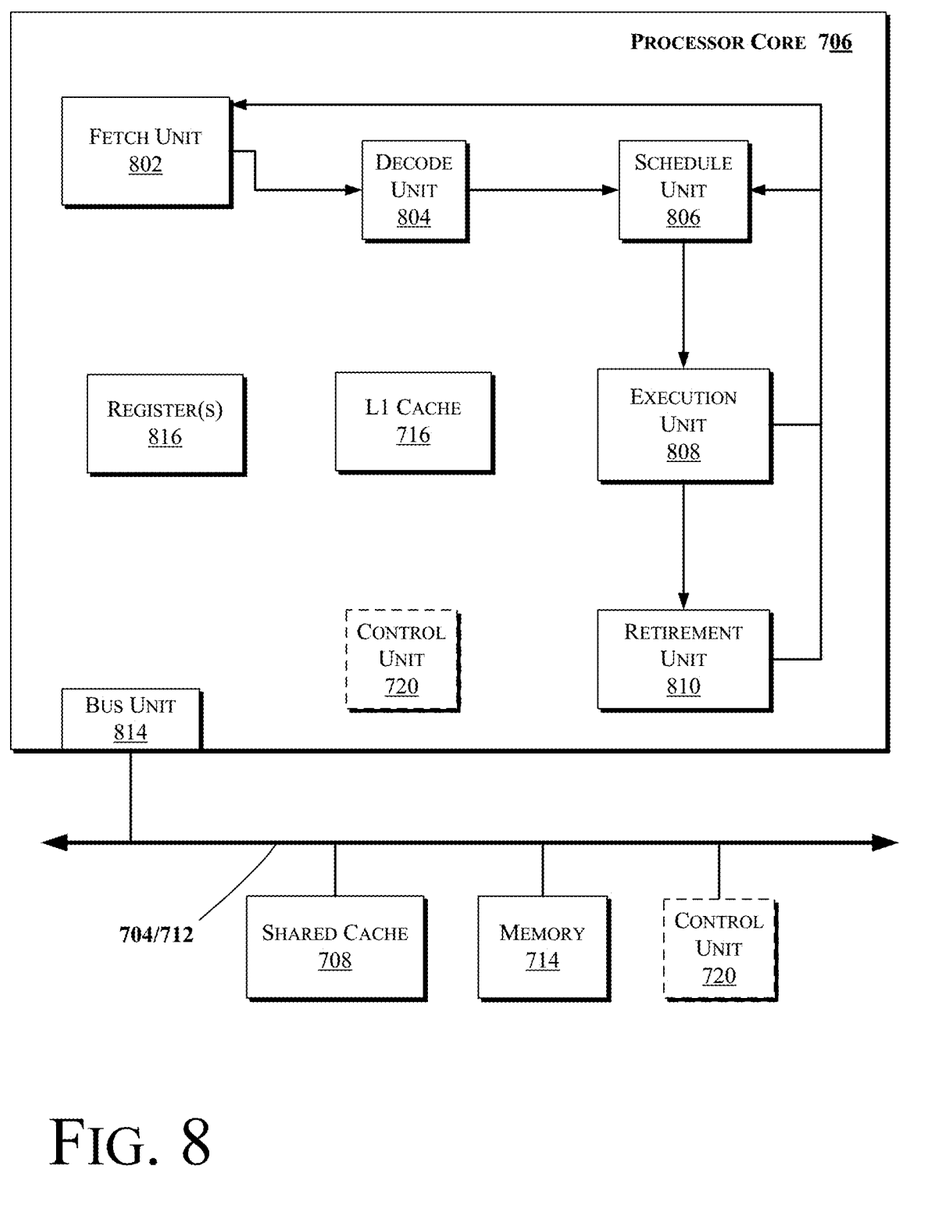

FIG. 8 illustrates a block diagram of portions of a processor core 706 and other components of a computing system, according to an example. In one example, the arrows shown in FIG. 8 illustrate the flow direction of instructions through the core 706. One or more processor cores (such as the processor core 706) may be implemented on a single integrated circuit chip (or die) such as discussed with reference to FIG. 7. Moreover, the chip may include one or more shared and/or private caches (e.g., cache 708 of FIG. 7), interconnections (e.g., interconnections 704 and/or 112 of FIG. 7), control units, memory controllers, or other components.

As illustrated in FIG. 8, the processor core 706 may include a fetch unit 802 to fetch instructions (including instructions with conditional branches) for execution by the core 706. The instructions may be fetched from any storage devices such as the memory 714. The core 706 may also include a decode unit 804 to decode the fetched instruction. For instance, the decode unit 804 may decode the fetched instruction into a plurality of uops (micro-operations).

Additionally, the core 706 may include a schedule unit 806. The schedule unit 806 may perform various operations associated with storing decoded instructions (e.g., received from the decode unit 804) until the instructions are ready for dispatch, e.g., until all source values of a decoded instruction become available. In one example, the schedule unit 806 may schedule and/or issue (or dispatch) decoded instructions to an execution unit 808 for execution. The execution unit 808 may execute the dispatched instructions after they are decoded (e.g., by the decode unit 804) and dispatched (e.g., by the schedule unit 806). In an example, the execution unit 808 may include more than one execution unit. The execution unit 808 may also perform various arithmetic operations such as addition, subtraction, multiplication, and/or division, and may include one or more an arithmetic logic units (ALUs). In an example, a co-processor (not shown) may perform various arithmetic operations in conjunction with the execution unit 808.

Further, the execution unit 808 may execute instructions out-of-order. Hence, the processor core 706 may be an out-of-order processor core in one example. The core 706 may also include a retirement unit 810. The retirement unit 810 may retire executed instructions after they are committed. In an example, retirement of the executed instructions may result in processor state being committed from the execution of the instructions, physical registers used by the instructions being de-allocated, etc.

The core 706 may also include a bus unit 714 to enable communication between components of the processor core 706 and other components (such as the components discussed with reference to FIG. 8) via one or more buses (e.g., buses 804 and/or 812). The core 706 may also include one or more registers 816 to store data accessed by various components of the core 706 (such as values related to power consumption state settings).

Furthermore, even though FIG. 7 illustrates the control unit 720 to be coupled to the core 706 via interconnect 812, in various examples the control unit 720 may be located elsewhere such as inside the core 706, coupled to the core via bus 704, etc.

Figure 9:
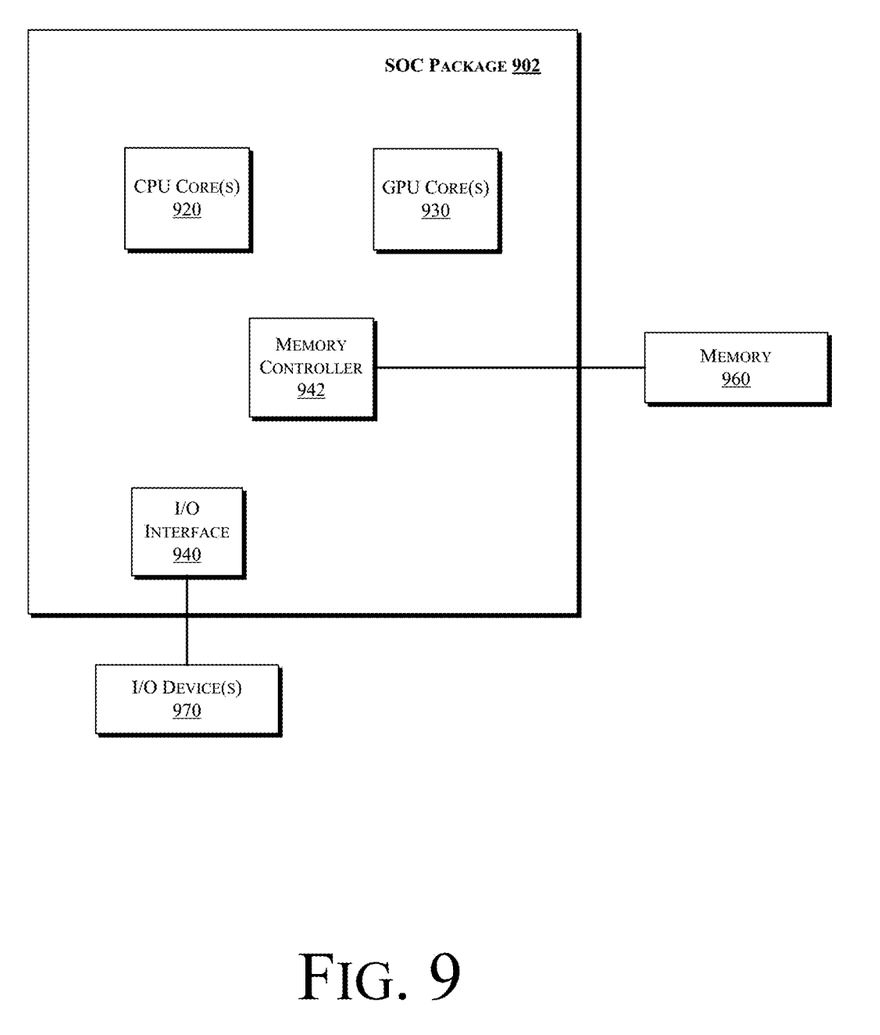

In some examples, one or more of the components discussed herein can be embodied as a System On Chip (SOC) device. FIG. 9 illustrates a block diagram of an SOC package in accordance with an example. As illustrated in FIG. 9, SOC 902 includes one or more processor cores 920, one or more graphics processor cores 930, an Input/Output (I/O) interface 940, and a memory controller 942. Various components of the SOC package 902 may be coupled to an interconnect or bus such as discussed herein with reference to the other figures. Also, the SOC package 902 may include more or less components, such as those discussed herein with reference to the other figures. Further, each component of the SOC package 902 may include one or more other components, e.g., as discussed with reference to the other figures herein. In one example, SOC package 902 (and its components) is provided on one or more Integrated Circuit (IC) die, e.g., which are packaged into a single semiconductor device.

As illustrated in FIG. 9, SOC package 902 is coupled to a memory 960 (which may be similar to or the same as memory discussed herein with reference to the other figures) via the memory controller 942. In an example, the memory 960 (or a portion of it) can be integrated on the SOC package 902.

The I/O interface 940 may be coupled to one or more I/O devices 970, e.g., via an interconnect and/or bus such as discussed herein with reference to other figures. I/O device (s) 970 may include one or more of a keyboard, a mouse, a touchpad, a display, an image/video capture device (such as a camera or camcorder/video recorder), a touch surface, a speaker, or the like.

Figure 10:
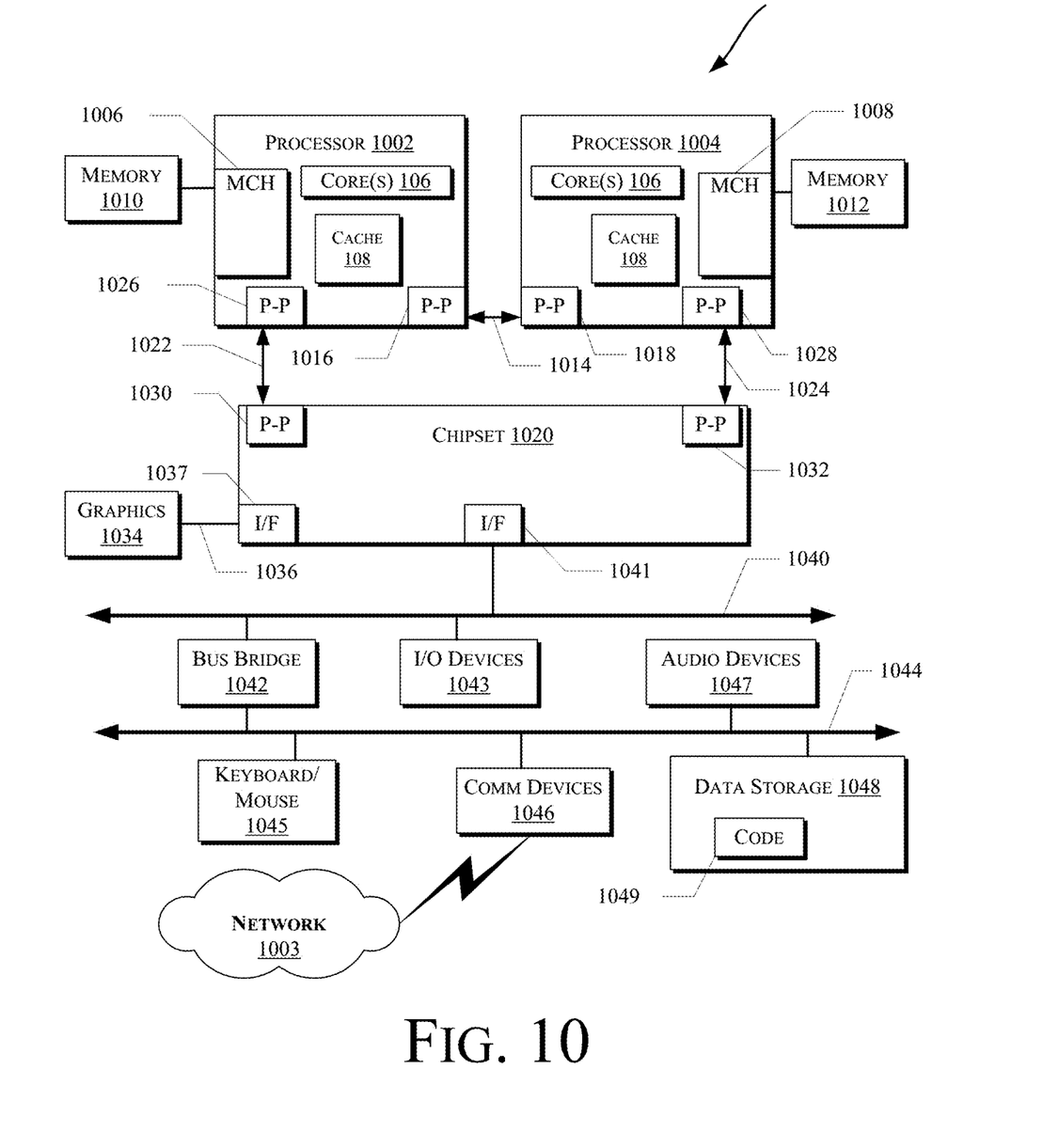

FIG. 10 illustrates a computing system 1000 that is arranged in a point-to-point (PtP) configuration, according to an example. In particular, FIG. 10 shows a system where processors, memory, and input/output devices are interconnected by a number of point-to-point interfaces. The operations discussed with reference to FIG. 2 may be performed by one or more components of the system 1000.

As illustrated in FIG. 10, the system 1000 may include several processors, of which only two, processors 1002 and 1004 are shown for clarity. The processors 1002 and 1004 may each include a local memory controller hub (MCH) 1006 and 1008 to enable communication with memories 1010 and 1012. MCH 1006 and 1008 may include the memory controller 120 and/or logic 125 of FIG. 1 in some examples.

In an example, the processors 1002 and 1004 may be one of the processors 702 discussed with reference to FIG. 7. The processors 1002 and 1004 may exchange data via a point-to-point (PtP) interface 1014 using PtP interface circuits 1016 and 1018, respectively. Also, the processors 1002 and 1004 may each exchange data with a chipset 1020 via individual PtP interfaces 1022 and 1024 using point-to-point interface circuits 1026, 1028, 1030, and 1032. The chipset 1020 may further exchange data with a high-performance graphics circuit 1034 via a high-performance graphics interface 1036, e.g., using a PtP interface circuit 1037.

As shown in FIG. 10, one or more of the cores 106 and/or cache 108 of FIG. 1 may be located within the processors 1004. Other examples, however, may exist in other circuits, logic units, or devices within the system 1000 of FIG. 10. Furthermore, other examples may be distributed throughout several circuits, logic units, or devices illustrated in FIG. 10.

The chipset 1020 may communicate with a bus 1040 using a PtP interface circuit 1041. The bus 1040 may have one or more devices that communicate with it, such as a bus bridge 1042 and I/O devices 1043. Via a bus 1044, the bus bridge 1043 may communicate with other devices such as a keyboard/mouse 1045, communication devices 1046 (such as modems, network interface devices, or other communication devices that may communicate with the computer network 1003), audio I/O device, and/or a data storage device 1048. The data storage device 1048 (which may be a hard disk drive or a NAND flash based solid state drive) may store code 1049 that may be executed by the processors 1004.

The following examples pertain to further examples.

Example 1 is an apparatus, comprising a motion sensor to generate motion data, a controller comprising logic, at least partially including hardware logic, to sample the motion data at a predetermined sampling rate, apply a bias elimination algorithm to the motion data to generate an unbiased motion data set, and a transmitter to transmit the unbiased motion data set.

In Example 2, the subject matter of Example 1 can optionally include an arrangement in which the controller samples the motion data at a rate of 20 Hz.

In Example 3, the subject matter of any one of Examples 1-2 can optionally include an arrangement in which the bias estimation algorithm is applied to a collection of 400 samples.

In Example 4, the subject matter of any one of Examples 1-3 can optionally include logic, at least partially including hardware logic, configured to generate a fast fourier transform (FFT) of the motion tracking data, eliminate at least one coefficient from the FFT to generate a simplified FFT and reconstruct the motion tracking data by applying an inverse fast fourier transform (IFFT) to the simplified FFT.

In Example 5, the subject matter of any one of Examples 1-4 can optionally include an input/output interface to receive motion tracking data from at least one remote motion sensing device, and a controller coupled to the input/output interface and comprising logic, at least partially including hardware logic, to receive the motion tracking data, generate estimated position data using the motion tracking data, and present the estimated position data on a display device coupled to the electronic device.

In Example 7, the subject matter of any on of Examples 1-6 can optionally include logic, at least partly including hardware logic, to render a video which comprises the estimated position data on the display device.

Example 8 is a controller comprising logic, at least partially including hardware logic, to sample motion data from a motion sensor at a predetermined sampling rate, apply a bias elimination algorithm to the motion data to generate an unbiased motion data set, and forward the unbiased motion data set to a transmitter coupled to the controller to transmit the unbiased motion data set.

In Example 9, the subject matter of Example 8 can optionally include an arrangement in which the controller samples the motion data at a rate of 20 Hz.

In Example 10, the subject matter of any one of Examples 8-9 can optionally include an arrangement in which the bias estimation algorithm is applied to a collection of 400 samples:

In Example 11, the subject matter of any one of Examples 8-10 can optionally include logic, at least partially including hardware logic, to generate a fast fourier transform (FFT) of the motion tracking data, eliminate at least one coefficient from the FFT to generate a simplified FFT and reconstruct the motion tracking data by applying an inverse fast fourier transform (IFFT) to the simplified FFT.

In Example 12, the subject matter of any one of Examples 8-11 can optionally include an electronic device communicatively coupled to the controller and comprising an input/output interface to receive motion tracking data from at least one remote motion sensing device, and a controller coupled to the input/output interface and comprising logic, at least partially including hardware logic, to receive the motion tracking data, generate estimated position data using the motion tracking data, and present the estimated position data on a display device coupled to the electronic device.

In Example 13 the subject matter of Example 12 can optionally include logic, at least partially including hardware logic, to apply a Kalman Filter algorithm to the motion tracking data.

In Example 14, the subject matter of any one of Examples 12-13 can optionally include an arrangement in which the controller in the electronic device comprises logic, at least partially including hardware logic, to render a video which comprises the estimated position data on the display device.

Example 15 is an electronic device, comprising an input/output interface to receive motion tracking data from at least one remote motion sensing device, and a controller coupled to the input/output interface and comprising logic, at least partially including hardware logic, to receive the motion tracking data, generate estimated position data using the motion tracking data; and present the estimated position data on a display device coupled to the electronic device.

In Example 16 the subject matter of Example 15 can optionally include logic, at least partially including hardware logic, to apply a Kalman Filter algorithm to the motion tracking data.

In Example 17, the subject matter of any one of Examples 15-16 can optionally include an arrangement in which the controller in the electronic device comprises logic, at least partially including hardware logic, to render a video which comprises the estimated position data on the display device.

Example 18 is a controller comprising logic, at least partially including hardware logic, to receive motion tracking data, generate estimated position data using the motion tracking data and present the estimated position data on a display device coupled to the electronic device.

In Example 19 the subject matter of Example 18 can optionally include logic, at least partially including hardware logic, to apply a Kalman Filter algorithm to the motion tracking data.

In Example 20, the subject matter of any one of Examples 18-19 can optionally include an arrangement in which the controller comprises logic, at least partially including hardware logic, to generate a fast fourier transform (FFT) of the motion tracking data, eliminate at least one coefficient from the FFT to generate a simplified FFT and reconstruct the motion tracking data by applying in inverse fast fourier transform (IFFT) to the simplified FFT.

In Example 21, the subject matter of any one of Examples 18-20 can optionally include an arrangement in which the controller in the electronic device comprises logic, at least partially including hardware logic, to render a video which comprises the estimated position data on the display device.

The terms "logic instructions" as referred to herein relates to expressions which may be understood by one or more machines for performing one or more logical operations. For example, logic instructions may comprise instructions which are interpretable by a processor compiler for executing one or more operations on one or more data objects. However, this is merely an example of machine-readable instructions and examples are not limited in this respect.

The terms "computer readable medium" as referred to herein relates to media capable of maintaining expressions which are perceivable by one or more machines. For example, a computer readable medium may comprise one or more storage devices for storing computer readable instructions or data. Such storage devices may comprise storage media such as, for example, optical, magnetic or semiconductor storage media. However, this is merely an example of a computer readable medium and examples are not limited in this respect.

The term "logic" as referred to herein relates to structure for performing one or more logical operations. For example, logic may comprise circuitry which provides one or more output signals based upon one or more input signals. Such circuitry may comprise a finite state machine which receives a digital input and provides a digital output, or circuitry which provides one or more analog output signals in response to one or more analog input signals. Such circuitry may be provided in an application specific integrated circuit (ASIC) or field programmable gate array (FPGA). Also, logic may comprise machine-readable instructions stored in a memory in combination with processing circuitry to execute such machine-readable instructions. However, these are merely examples of structures which may provide logic and examples are not limited in this respect.

Some of the methods described herein may be embodied as logic instructions on a computer-readable medium. When executed on a processor, the logic instructions cause a processor to be programmed as a special-purpose machine that implements the described methods. The processor, when configured by the logic instructions to execute the methods described herein, constitutes structure for performing the described methods. Alternatively, the methods described herein may be reduced to logic on, e.g., a field programmable gate array (FPGA), an application specific integrated circuit (ASIC) or the like.

In the description and claims, the terms coupled and connected, along with their derivatives, may be used. In particular examples, connected may be used to indicate that two or more elements are in direct physical or electrical contact with each other. Coupled may mean that two or more elements are in direct physical or electrical contact. However, coupled may also mean that two or more elements may not be in direct contact with each other, but yet may still cooperate or interact with each other.

Reference in the specification to "one example" or "some examples" means that a particular feature, structure, or characteristic described in connection with the example is included in at least an implementation. The appearances of the phrase "in one example" in various places in the specification may or may not be all referring to the same example.

Although examples have been described in language specific to structural features and/or methodological acts, it is to be understood that claimed subject matter may not be limited to the specific features or acts described. Rather, the specific features and acts are disclosed as sample forms of implementing the claimed subject matter.

The invention claimed is:

1. An apparatus, comprising:
    a motion sensor to generate motion data;
    a controller comprising logic, at least partially including hardware logic, to:
        sample the motion data at a predetermined sampling rate;
        apply a bias elimination algorithm to the motion data to generate an unbiased motion data set;
        generate a fast fourier transform (FFT) of the motion tracking data; and
        eliminate at least one coefficient from the FFT to generate a simplified FFT; and
        reconstruct the motion tracking data by applying an inverse fast fourier transform (IFFT) to the simplified FFT; and
    a transmitter to transmit the unbiased motion data set.

2. The apparatus of claim 1, wherein the controller samples the motion data at a rate of 20 Hz.

3. The apparatus of claim 2, wherein the bias estimation algorithm is applied to a collection of 400 samples.

4. The apparatus of claim 1, further comprising an electronic device communicatively coupled to the apparatus and comprising:
an input/output interface to receive motion tracking data from at least one remote motion sensing device; and
a processor coupled to the input/output interface and comprising logic, at least partially including hardware logic, to:
receive the motion tracking data;
generate estimated position data using the motion tracking data; and
present the estimated position data on a display device coupled to the electronic device.

5. The apparatus of claim 4, wherein the controller in the electronic device comprises logic, at least partially including hardware logic, to:
apply a Kalman Filter algorithm to the motion tracking data.

6. The apparatus of claim 1, wherein the controller in the electronic device comprises logic, at least partially including hardware logic, to:
render a video which comprises the estimated position data on the display device.

7. A controller comprising logic, at least partially including hardware logic, to:
sample motion data from a motion sensor at a predetermined sampling rate;
apply a bias elimination algorithm to the motion data to generate an unbiased motion data set;
generate a fast fourier transform (FFT) of the motion tracking data; and
eliminate at least one coefficient from the FFT to generate a simplified FFT; and
reconstruct the motion tracking data by applying an inverse fast fourier transform (IFFT) to the simplified FFT; and
forward the unbiased motion data set to a transmitter coupled to the controller to transmit the unbiased motion data set.

8. The controller of claim 7, wherein the controller samples the motion data at a rate of 20 Hz.

9. The controller of claim 8, wherein the bias estimation algorithm is applied to a collection of 400 samples.

10. The controller of claim 7, further comprising an electronic device communicatively coupled to the controller and comprising:
an input/output interface to receive motion tracking data from at least one remote motion sensing device; and
a controller coupled to the input/output interface and comprising logic, at least partially including hardware logic, to:
receive the motion tracking data;
generate estimated position data using the motion tracking data; and
present the estimated position data on a display device coupled to the electronic device.

11. The controller of claim 10, wherein the controller in the electronic device comprises logic, at least partially including hardware logic, to:
apply a Kalman Filter algorithm to the motion tracking data.

12. The controller of claim 11, wherein the controller in the electronic device comprises logic, at least partially including hardware logic, to:
render a video which comprises the estimated position data on the display device.

13. An electronic device, comprising:
an input/output interface to receive motion tracking data from at least one remote motion sensing device; and
a controller coupled to the input/output interface and comprising logic, at least partially including hardware logic, to:
receive the motion tracking data;
generate estimated position data using the motion tracking data;
generate a fast fourier transform (FFT) of the motion tracking data; and
eliminate at least one coefficient from the FFT to generate a simplified FFT; and
reconstruct the motion tracking data by applying an inverse fast fourier transform (IFFT) to the simplified FFT; and
present the estimated position data on a display device coupled to the electronic device.

14. The electronic device of claim 13, wherein the controller comprises logic, at least partially including hardware logic, to:
apply a Kalman Filter algorithm to the motion tracking data.

15. The electronic device of claim 14, wherein the controller comprises logic, at least partially including hardware logic, to:
render a video which comprises the estimated position data on the display device.

16. A controller comprising logic, at least partially including hardware logic, to:
receive motion tracking data;
generate estimated position data using the motion tracking data;
generate a fast fourier transform (FFT) of the motion tracking data; and
eliminate at least one coefficient from the FFT to generate a simplified FFT; and
reconstruct the motion tracking data by applying an inverse fast fourier transform (IFFT) to the simplified FFT; and
present the estimated position data on a display device coupled to the electronic device.

17. The controller of claim 16, wherein the controller comprises logic, at least partially including hardware logic, to:
render a video which comprises the estimated position data on the display device.

* * * * *